United States Patent
Chen

(10) Patent No.: US 10,642,368 B2
(45) Date of Patent: May 5, 2020

(54) BODY POSTURE DETECTION SYSTEM, SUIT AND METHOD

(71) Applicant: HTC Corporation, Taoyuan (TW)

(72) Inventor: Yuan-Tung Chen, Taoyuan (TW)

(73) Assignee: HTC Corporation, Taoyuan (TW)

( * ) Notice: Subject to any disclaimer, the term of this patent is extended or adjusted under 35 U.S.C. 154(b) by 39 days.

(21) Appl. No.: 15/818,771

(22) Filed: Nov. 21, 2017

(65) Prior Publication Data

US 2018/0143696 A1 May 24, 2018

Related U.S. Application Data

(60) Provisional application No. 62/424,555, filed on Nov. 21, 2016.

(51) Int. Cl.
| | |
|---|---|
| *G06F 3/01* | (2006.01) |
| *G01S 15/08* | (2006.01) |
| *G06F 3/0346* | (2013.01) |
| *G01P 13/00* | (2006.01) |

(Continued)

(52) U.S. Cl.
CPC .............. *G06F 3/017* (2013.01); *G01P 13/00* (2013.01); *G01S 11/14* (2013.01); *G01S 15/08* (2013.01); *G06F 3/011* (2013.01); *G06F 3/0346* (2013.01); *A61B 5/6805* (2013.01); *G06F 3/01* (2013.01)

(58) Field of Classification Search
CPC ........ G06F 3/017; G06F 3/011; G06F 3/0346; G06G 3/011; G01P 13/00; G01S 11/14; A61B 5/6805
See application file for complete search history.

(56) References Cited

U.S. PATENT DOCUMENTS

2008/0223131 A1 9/2008 Vannucci et al.
2008/0319349 A1* 12/2008 Zilberman ........... A61B 5/0031
600/587

(Continued)

FOREIGN PATENT DOCUMENTS

| EP | 3067783 A1 | 9/2016 |
| TW | I509454 B | 11/2015 |
| WO | 2014114967 A1 | 7/2014 |

OTHER PUBLICATIONS

Corresponding Taiwan office action dated Aug. 6, 2018.
Corresponding extended European search report dated Mar. 26, 2018.

*Primary Examiner* — Kent W Chang
*Assistant Examiner* — Sujit Shah
(74) *Attorney, Agent, or Firm* — CKC & Partners Co., LLC

(57) ABSTRACT

A body posture detection system includes an inertial measurement unit, at least two ultrasonic transceivers and a processor. The inertial measurement unit is configured to retrieve an orientation vector of a first portion of a human body. The ultrasonic transceivers are mounted on the first portion and a second portion of the human body respectively. The processor is configured to generate a candidate gesture range of the first portion according to the orientation vector. The processor is configured to measure a distance between the first portion and the second portion according to an ultrasound transmitted between the ultrasonic transceivers. The processor is further configured to determine a current gesture of the first portion from the candidate gesture range according to the distance.

16 Claims, 11 Drawing Sheets

(51) Int. Cl.
*G01S 11/14* (2006.01)
*A61B 5/00* (2006.01)

(56) References Cited

U.S. PATENT DOCUMENTS

| | | | |
|---|---|---|---|
| 2013/0158946 A1* | 6/2013 | Scherberger | G06F 3/014 |
| | | | 702/151 |
| 2015/0366504 A1* | 12/2015 | Connor | A61B 5/6804 |
| | | | 600/301 |
| 2016/0015299 A1 | 1/2016 | Chan et al. | |
| 2016/0154241 A1* | 6/2016 | Alhashim | G02B 27/0172 |
| | | | 345/8 |
| 2016/0162022 A1* | 6/2016 | Seth | G06F 3/017 |
| | | | 345/156 |
| 2016/0256082 A1* | 9/2016 | Ely | A61B 5/0024 |
| 2016/0299570 A1* | 10/2016 | Davydov | G06F 1/163 |
| 2016/0335487 A1* | 11/2016 | Ming | G06K 9/00335 |
| 2017/0060250 A1* | 3/2017 | Nayak | G06F 3/017 |

* cited by examiner

BODY POSTURE DETECTION SYSTEM, SUIT AND METHOD

CROSS-REFERENCE TO RELATED APPLICATION

This application claims priority to U.S. Provisional Application Ser. No. 62/424,555, filed on Nov. 21, 2016, which is herein incorporated by reference.

BACKGROUND

Field of Invention

Present disclosure relates to a detection system, suit and method. More particularly, present disclosure relates to a body posture detection system, a body posture detection suit and a body posture detection method.

Description of Related Art

There are many ways to detect human body postures. A detection system equipped with multiple inertial measurement units (IMUs) is one of the many ways. However, since the detection of IMUs is based on the reference of gravity, the accuracy of existing detection suits configured with IMUs can be impacted by the magnetic fields generated by reinforcement steels used in modern buildings. When such a detection suit is applied in an indoor space, its accuracy drops dramatically.

Apparently, existing human body detection systems are extremely limited by spaces where they were applied. Therefore, improvements are required.

SUMMARY

Aiming to solve aforementioned problems, the present disclosure provides a body posture detection system, a body posture detection suit and a body posture detection method.

The present disclosure provides a body posture detection system. The body posture detection system comprises an inertial measurement unit, an ultrasonic module, and a processor. The inertial measurement unit is mounted on a first portion of a human body and is configured to sense an orientation vector of the first portion. The ultrasonic module comprises a first ultrasonic transceiver mounted on the first portion and a second ultrasonic transceiver mounted on a second portion of the human body. The processor is in communication with the inertial measurement unit and the ultrasonic module. The processor is configured to generate a candidate gesture range of the first portion according to the orientation vector sensed by the inertial measurement unit. The processor is configured to measure a distance between the first portion and the second portion according to an ultrasound transmitted between the first ultrasonic transceiver and the second ultrasonic transceiver. The processor is configured to determine a current gesture of the first portion from the candidate gesture range according to the distance measured from the ultrasound detected by the ultrasonic module.

The present disclosure provides a body posture detection suit. The body posture detection suit includes a torso fitting component, limb fitting components, inertial measurement units, ultrasonic transceivers and a processor. The limb fitting components are connected to the torso fitting component. The inertial measurement units are disposed on the torso fitting component and the limb fitting components respectively. The inertial measurement units are configured to sense orientation vectors of the torso fitting component or the limb fitting components. The ultrasonic transceivers are disposed on multiple reference points on the limb fitting components. The ultrasonic transceivers are configured to send ultrasounds and to receive the ultrasounds respectively. The processor is in communication with the inertial measurement units and the ultrasonic transceivers. The processor is configured to measure distances among these reference points according to flight times of the ultrasounds, retrieve the orientation vectors, and generate a current gesture of the limb fitting components in combination with the torso fitting component according to the orientation vectors and the distances.

Another aspect of the present disclosure is to provide a body posture detection method suitable for a human body. The body posture detection method comprises following operations. An orientation vector of a first portion of the human body is sensed by an inertial measurement unit. A distance between a first portion of the human body and a second portion of the human body is measured by a processor according to an ultrasound transmitted between a first ultrasonic transceiver mounted on the first portion and a second ultrasonic transceiver mounted on the second portion. A candidate gesture range of the first portion is generated by the processor according to the orientation vector sensed by the inertial measurement unit. A current gesture of the first portion is determined by the ultrasonic module from the candidate gesture range according to the distance.

It is to be understood that both the foregoing general description and the following detailed description are made by examples, and are intended to provide further explanation of the disclosure as claimed.

BRIEF DESCRIPTION OF THE DRAWINGS

Present disclosure can be more fully understood by reading the following detailed description of the embodiments, with reference made to the accompanying drawings as follows.

DETAILED DESCRIPTION

Figure 1:
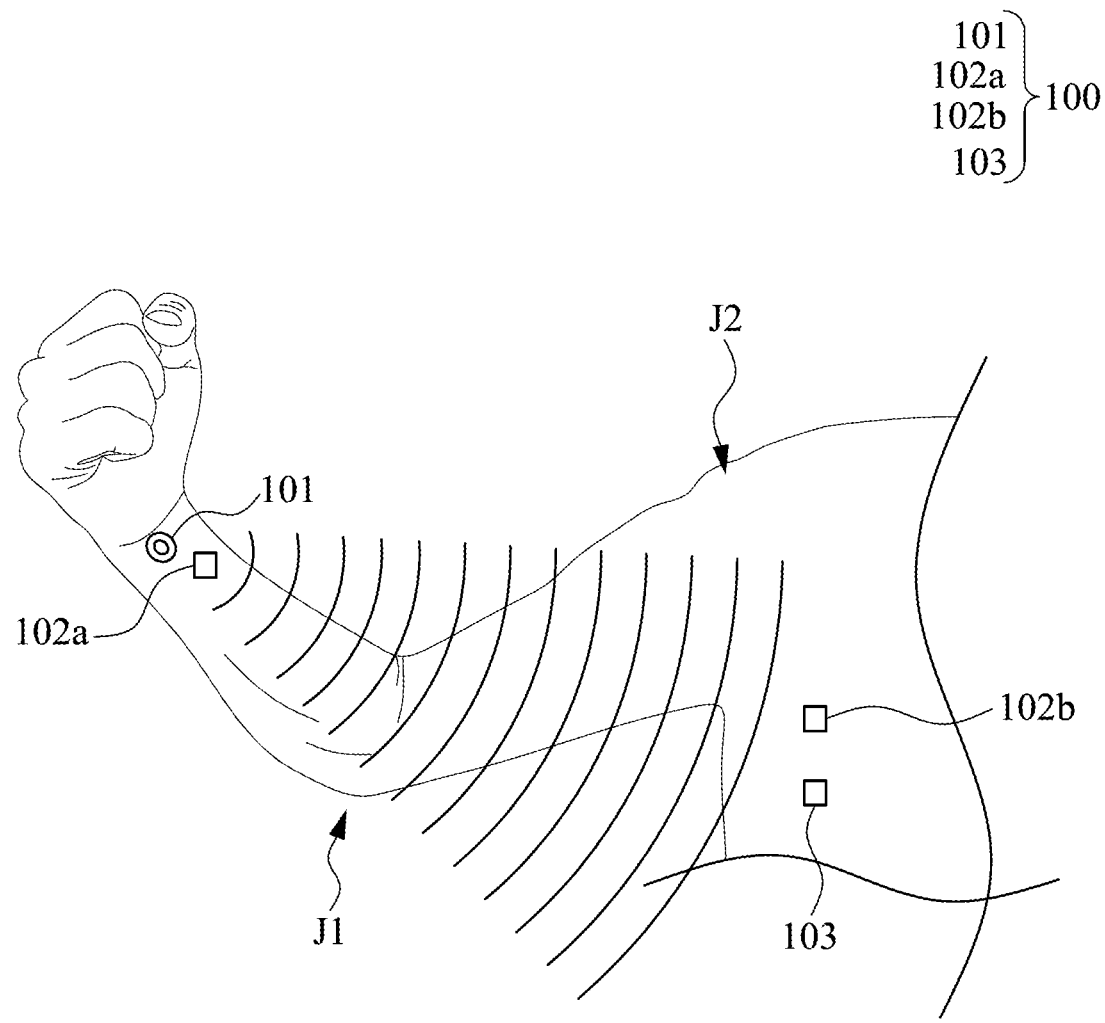
FIG. 1 is a schematic diagram of a body posture detection system illustrated according to one embodiment of the present disclosure.

Reference will now be made in detail to the embodiments of the present disclosure, examples of which are illustrated in the accompanying drawings. Wherever possible, the same reference numbers are used in the drawings and the description to refer to the same or like parts.

The terms used in this specification generally have their ordinary meanings in the art and in the specific context where each term is used. The use of examples in this specification, including examples of any terms discussed herein, is illustrative only, and in no way limits the scope and meaning of the disclosure or of any exemplified term. Likewise, the present disclosure is not limited to various embodiments given in this specification.

As used herein, the terms "comprising," "including," "having," and the like are to be understood to be open-ended, i.e., to mean including but not limited to.

Reference throughout the specification to "one embodiment" or "an embodiment" means that a particular feature, structure, implementation, or characteristic described in connection with the embodiment is included in at least one embodiment of the present disclosure. Thus, uses of the phrases "in one embodiment" or "in an embodiment" in various places throughout the specification are not necessarily all referring to the same embodiment. Furthermore, the particular features, structures, implementation, or characteristics may be combined in any suitable manner in one or more embodiments.

In the following description and claims, the terms "coupled" and "connected", along with their derivatives, may be used. In particular embodiments, "connected" and "coupled" may be used to indicate that two or more elements are in direct physical or electrical contact with each other, or may also mean that two or more elements may be in indirect contact with each other. "Coupled" and "connected" may still be used to indicate that two or more elements cooperate or interact with each other.

FIG. 1 is a schematic diagram of a body posture detection system illustrated according to one embodiment of the present disclosure. In the embodiment, the body posture detection system 100 is deployed on a user's body, especially a limb. The body posture detection system 100 comprises an inertial measurement unit 101, a first ultrasonic transceiver 102a, a second ultrasonic transceiver 102b and a processor 103. The inertial measurement unit 101, the first ultrasonic transceiver 102a, and the second ultrasonic transceiver 102b are in communication with the processor 103 via a network, such as Wi-Fi or Bluetooth, so that the components are capable of interchanging information with the processor 103. In some embodiments, the inertial measurement unit 101, the first ultrasonic transceiver 102a, the second ultrasonic transceiver 102b and the processor 103 are all in communication via the network. That allows the components to interchange information with each other.

In an embodiment, the inertial measurement unit 101, deployed on an end point of a user's arm, is a sensor circuit including a combination of a 3-axis accelerometer and a 3-axis gyroscope. The 3-axis accelerometer is configured to measure linear accelerations on the end of the arm, and the 3-axis gyroscope is configured to measure angular velocities on the end of the arm. The inertial measurement unit 101 can detect an orientation vector of the user's arm when the arm is moving. The first ultrasonic transceiver 102a, deployed on a first reference point on the user's arm, is configured to broadcast a first ultrasonic wave and to receive ultrasonic waves from other ultrasound source. The second ultrasonic transceiver 102b is deployed on a second reference point on the user's torso and is configured to broadcast a second ultrasonic wave and to receive ultrasonic waves from other ultrasound source. In an embodiment, the first ultrasonic wave and second ultrasonic wave are unique and different from each other (e.g., the first ultrasonic wave and second ultrasonic wave are broadcasted at different sound frequencies, different amplitudes or different waveform pattern), so that the ultrasonic transceivers are able to distinguish origins of these ultrasonic waves from each other. In another embodiment, the first ultrasonic wave and second ultrasonic wave are generated in a time-division way during different time periods with a similar format (e.g., in frequency, amplitude or waveform pattern), so that the ultrasonic transceivers are able to distinguish origins of these ultrasonic waves according to a time division of the received ultrasonic wave.

In an embodiment, the first reference point and the second reference point are located on different portions of a human body. In the embodiment shown in FIG. 1, the first reference point is located on a lower arm portion and the second reference point is located on a chest portion of the human body. The lower arm portion shall be movable relative to the chest portion according to a gesture or a posture of the human body. In this embodiment, the body posture detection system 100 is able to detect a relationship between these two portions, so as to recognize the gesture or the posture of the human body.

In the embodiment, the processor 103 includes, for example, a single processing unit or a combination of plurality microprocessors electrically connected to internal or external memory via buses. The internal or external memory includes volatile and non-volatile memories. The processor 103 is configured to fetch a set of instructions from internal or external memories, to execute the set of instructions, and to perform predetermined processes according to the instructions. The processor 103 can be attached to the user's body, or can be deployed in a range that is possible to communicate with the inertial measurement unit 101, the first ultrasonic transceiver 102a, and the second ultrasonic transceiver 102b. In some embodiment, the processor 103 can be a central processing unit contained by a mobile device or computer. As long as the processor 103 can interchange information with aforesaid components, the processor 103 can perform predetermined processes according to the instructions.

In the embodiment, the inertial measurement unit 101 is deployed on a critical node (e.g., a center point or an end point) of the user's arm, for example, it can be settled near the palm of the user or be held by the user. The first ultrasonic transceiver 102a is disposed on the first reference point located at the user's lower arm, and the second reference point whereon the second ultrasonic transceiver 102b is disposed is substantially located in front of the user's chest. Depending on kinematic constraints of human body, the deployment of the first ultrasonic transceiver 102a and the second ultrasonic transceiver 102b is subject to change slightly on different users. It is noted, the deployment of the first ultrasonic transceiver 102a and the second ultrasonic transceiver 102b is aiming to detect relative distance between the first reference point and the second reference point accurately. As such, people in the art can dispose these ultrasonic transceivers on the user's arm and torso in a manner that prevents those ultrasonic waves being blocked.

In the embodiment, as mentioned, the processor 103 in communication with the first ultrasonic transceiver 102a and the second ultrasonic transceiver 102b. In the embodiment, after the first ultrasonic transceiver 102a broadcasts the first ultrasonic wave, the first ultrasonic wave travels in the air, and then received by the second ultrasonic transceiver 102b in a length of time. According to the length of time, the processor 103 can measure a relative distance between the second ultrasonic transceiver 102b and the first ultrasonic transceiver 102a according to the ultrasound transmitted between the first ultrasonic transceiver and the second ultrasonic transceiver.

In an embodiment, the processor 103 includes a timer circuit. When the processor 103 triggers the first ultrasonic transceiver 102a to broadcast the first ultrasonic wave, the processor 103 sets up the timer circuit to count the flight time of the ultrasound. When the second ultrasonic transceiver 102b receives the first ultrasonic wave and then informs the processor 103 about the received first ultrasonic wave, the processor 103 stops the timer circuit. The flight time of the first ultrasonic wave is acquired by an accumulated time count by the timer circuit. The relative distance between the first reference point on a first portion of the human body and the second reference point on a second portion of the human body can be obtained by the processor 103 according to the flight time. When the flight time is longer, the relative distance is determined to be larger by the processor 103. When the flight time is shorter, the relative distance is determined to be narrower by the processor 103. In aforesaid example, timing of first ultrasonic transceiver 102a and the second ultrasonic transceiver 102b are synchronized by the processor 103 to calculate the flight time. However, the disclosure is not limited thereto. In another embodiment, the first ultrasonic transceiver 102a and the second ultrasonic transceiver 102b are synchronized with radio frequency transceivers or optical signal transceivers disposed on these two ultrasonic transceivers.

In the embodiment, as mentioned, the processor 103 in communication with these sensors is configured to fetch instructions from memories to perform following processes. The processor 103 can retrieve the orientation vector detected by the inertial measurement unit 101 and the relative distances measured according to the ultrasound. The orientation vector can be used to track a direction of the first portion (e.g., user's lower arm) of the human body with respect to the gravitation. According to the orientation vector of the first portion, the processor 103 can generate a candidate gesture range of the first portion. It should be noted, the candidate gesture range is a data set containing several potential possibilities that the user's lower arm may have positioned. As such, for the sake to narrow down the possibilities, more information is required. In some cases, the processor can import kinematic constraints of joints J1, J2 and the length of the use's arm to eliminate some candidates from the candidate gesture range. However, since a joint of a human limb can be rotated along several axes to perform many delicate gestures, the candidate gesture range can only be narrowed down to a certain range.

In the embodiment, the relative distances can be used to track how far the first reference point and the second reference point are located from each other. The processor 103 can confirm the distance between these reference points, and that allows the processor 103 to narrow down the candidate gesture range to a single result. It is to say, with a distance between the user's lower arm and the user's chest, the processor 103 can determine a current gesture of the user's lower arm from the candidate gesture range accurately.

In some embodiments, if the relative distances obtained by the first ultrasonic transceiver 102a and the second ultrasonic transceiver 102b are not enough to confirm where each portion of the user's arm is positioned, a third ultrasonic transceiver (not shown) can be used as an additional reference. In that case, the third ultrasonic transceiver can receive ultrasonic waves to measure relative distances between itself with the other two ultrasonic transceivers. The processor 103 may adjust the result of the current gesture of the user's arm according to the relative distances measured by the third ultrasonic transceiver. Apparently, with more ultrasonic transceivers, the result of the current gesture will be more accurate.

Figure 2:
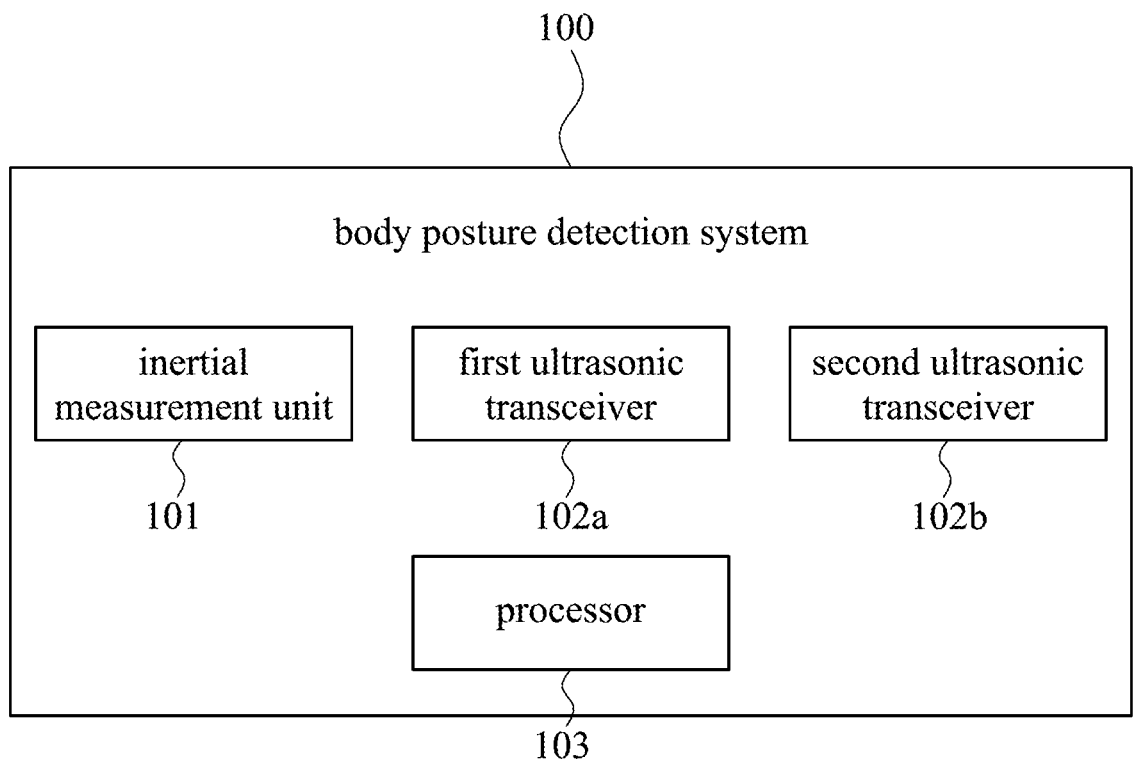
FIG. 2 is a schematic diagram of a body posture detection system illustrated according to one embodiment of the present disclosure.

FIG. 2 is a schematic diagram of a body posture detection system illustrated according to one embodiment of the present disclosure. In the embodiment, similar to aforementioned embodiment, a body posture detection system 100 having an inertial measurement unit 101, a first ultrasonic transceiver 102a, a second ultrasonic transceiver 102b and a processor 103 is shown in the figure. It should be noted, when the body posture detection system 100 is applied to a user, the manner that the units and transceivers deployed is similar to the embodiment shown in FIG. 1. However, it should be understood, in some embodiment of present disclosure, these units and transceivers of the body posture detection system 100 can be electrically connected via transmission lines, such as flat cable or twisted pairs. In that case, the transmission lines make the inertial measurement unit 101, the first ultrasonic transceiver 102a, the second ultrasonic transceiver 102b, and the processor 103 can communicate with each other. For example, when the first ultrasonic transceiver 102a generates the first ultrasonic wave, information regarding the sending time of the first ultrasonic wave can be transmit to the second ultrasonic transceiver 102b via one of the transmission lines. Therefore, the second ultrasonic transceiver 102b can measure the gap distance according to the information when the first ultrasonic wave is received. In another example, when the first ultrasonic transceiver 102a generates the first ultrasonic wave, the first ultrasonic transceiver 102a can transmit information regarding the sending time of the first ultrasonic wave to the processor 103 via one of the transmission lines. When the second ultrasonic transceiver 102b receives the first ultrasonic wave, the second ultrasonic transceiver 102b can transmit information regarding the receiving time of the first ultrasonic wave to the processor 103 via one of the transmission lines. The processor 103 can measure the relative distance between the first ultrasonic transceiver 102a and the second ultrasonic transceiver 102b according to information of the sending time and the receiving time.

Figure 3A:
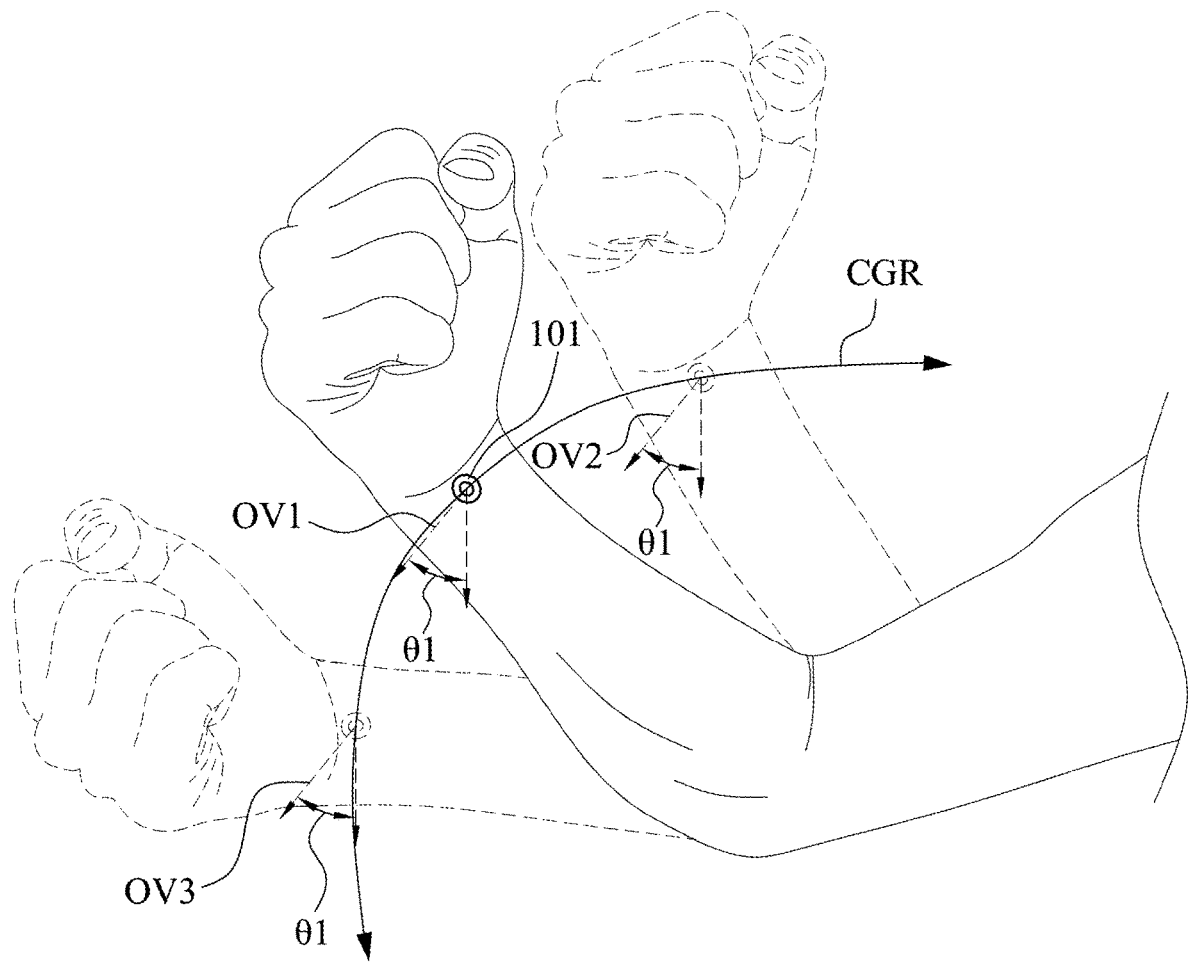
FIG. 3A is a schematic diagram of a candidate gesture range illustrated according to one embodiment of the present disclosure.

FIG. 3A is a schematic diagram of a candidate gesture range illustrated according to one embodiment of the present disclosure. In the embodiment, a user's arm is illustrated in FIG. 3A. It can be seen in the figure that the user can bend his arm to make his elbow turn horizontally. As mentioned, the inertial measurement unit 101 can be disposed on the wrist of the user to measure the orientation vector OV1-OV3 of the user's wrist. In this case, the orientation vectors OV1-OV3 are detected by the inertial measurement unit 101 to indicate geometric normal lines extended from the measurement unit 101. As shown in FIG. 3A, the user can make several gestures with his lower arm, but the orientation vectors detected by the measurement unit 101 all shows that angles 81 between the orientation vectors OV1-OV3 and the gravitation are the same. Therefore, in this case, the orientation vectors OV1-OV3 measured by the inertial measurement unit 101 is unable to provide information to confirm a current gesture among multiple possible positions as shown in FIG. 3A on the user's lower arm. The processor 103 (shown in FIG. 1) can only result in a candidate gesture range CGR of the user's lower arm, which is shown by the curve illustrated in the figure. It is to say, by using the inertial measurement unit 101 solely in a calculation of human body posture will lead to multiple solutions.

Figure 3B:
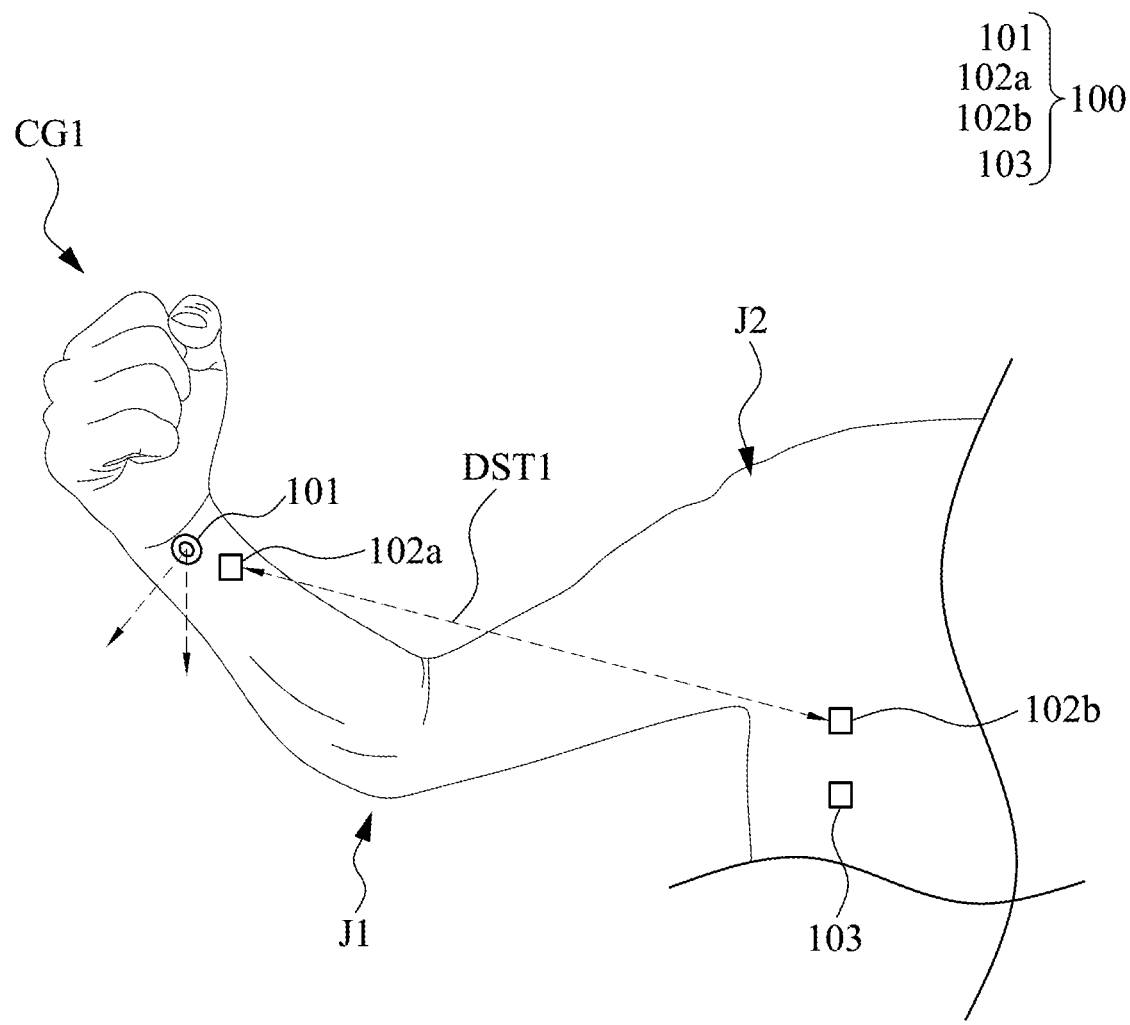
FIG. 3B is a schematic diagram of a body posture detection system illustrated according to the embodiment of FIG. 3A.

FIG. 3B is a schematic diagram of a body posture detection system illustrated according to the embodiment of FIG. 3A. In the embodiment, the user's arm illustrated in FIG. 3A is shown again. However, it can be seen in the figure, the first ultrasonic transceiver 102a disposed around the user's wrist can send the first ultrasonic wave to the second ultrasonic transceiver 102b disposed one the user's chest, therefore a first distance DST1 between these portions can be measured by the processor 103 in accordance with the flight time of the first ultrasonic wave. As such, the processor 103 (shown in FIG. 1) can select a potential candidate from the candidate gesture range CGR shown in FIG. 3A as a first current gesture CG1. Moreover, as mentioned, the kinematic constraints of the joint J1 and J2 can be imported for a more accurate determination of the first current gesture CG1.

Figure 3C:
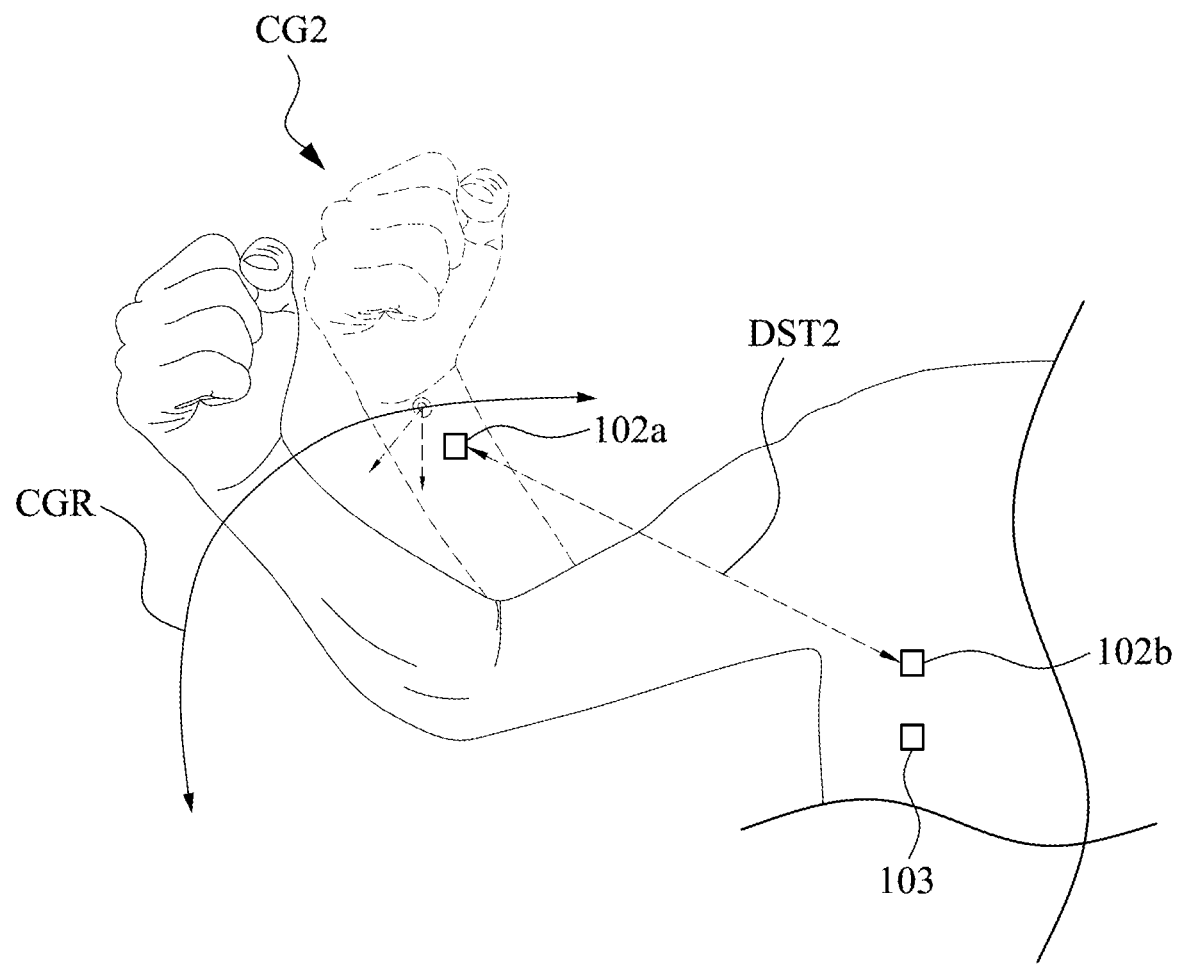
FIG. 3C is a schematic diagram of a body posture detection system illustrated according to the embodiment of FIG. 3A.

FIG. 3C is a schematic diagram of a body posture detection system illustrated according to the embodiment of FIG. 3A. In the embodiment, the user's arm illustrated in FIG. 3A is shown again. In the same manner, the first ultrasonic transceiver 102a disposed around the user's wrist can send the first ultrasonic wave to the second ultrasonic transceiver 102b disposed one the user's chest, and the processor 103 can measure a second distance DST2 between these portions with the flight time of the first ultrasonic wave. As such, the processor 103 (shown in FIG. 1) can select a potential candidate from the candidate gesture range CGR shown in FIG. 3A as a second current gesture CG2. Since the second distance DST1 shown in FIG. 3B and the second distance DST2 shown in this figure are different, the processor 103 can accurately distinguish the second current gesture CG2 from the first current gesture CG1.

Figure 3D:
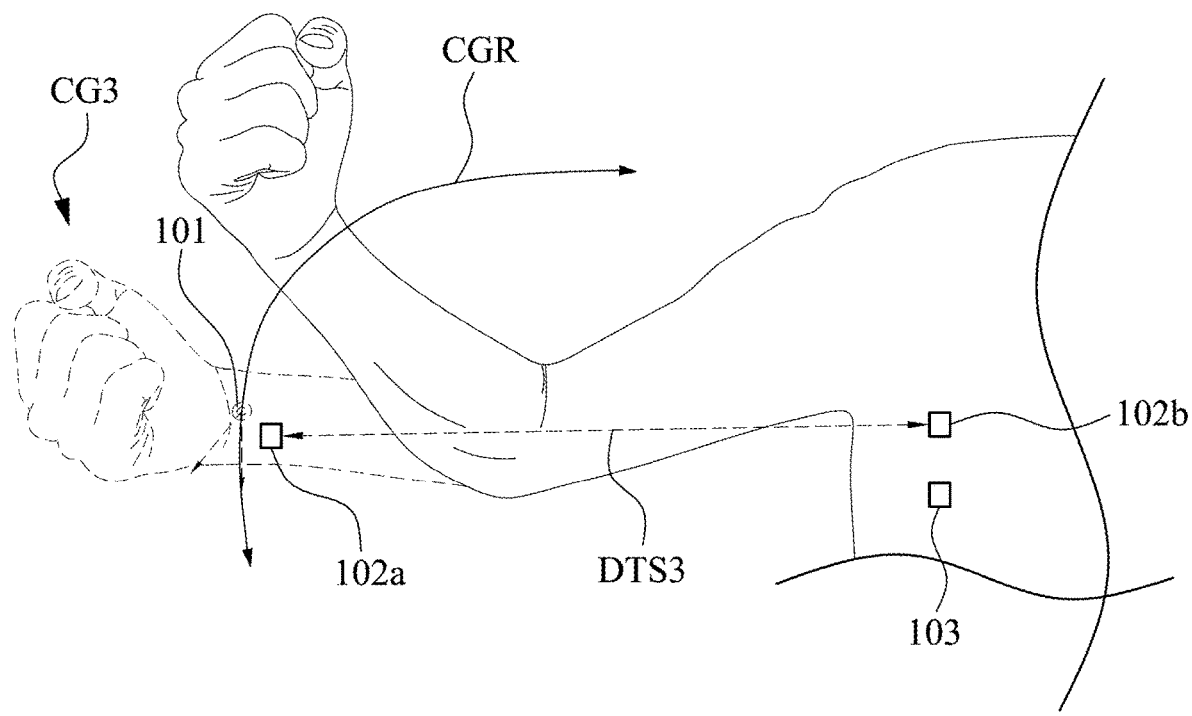
FIG. 3D is a schematic diagram of a body posture detection system illustrated according to the embodiment of FIG. 3A.

FIG. 3D is a schematic diagram of a body posture detection system illustrated according to the embodiment of FIG. 3A. In the embodiment, the user's arm illustrated in FIG. 3A is shown again. As mentioned, the first ultrasonic transceiver 102a disposed around the user's wrist can send the first ultrasonic wave to the second ultrasonic transceiver 102b disposed one the user's chest, and the processor 103 can measure a third distance DST3 between these portions with the flight time of the first ultrasonic wave. As such, the processor 103 (shown in FIG. 1) can select a potential candidate from the candidate gesture range CGR shown in FIG. 3A as a third current gesture CG3. Since third distance DST3 is apparently longer than the first distance DST1 and the second distance DST2 shown in aforesaid figures, the processor 103 can accurately distinguish the third current gesture CG3 with the other two current gestures.

As shown in FIG. 3A-3D, it apparently that present disclosure provides an approach to efficiently narrow down possible gestures of the user with the aid of ultrasonic transceivers. In other words, combining inertial measurement units with ultrasonic transceivers, present disclosure provides an efficient system that can reduce a multiple solution problem of human body posture to a singular solution problem.

Figure 4A:
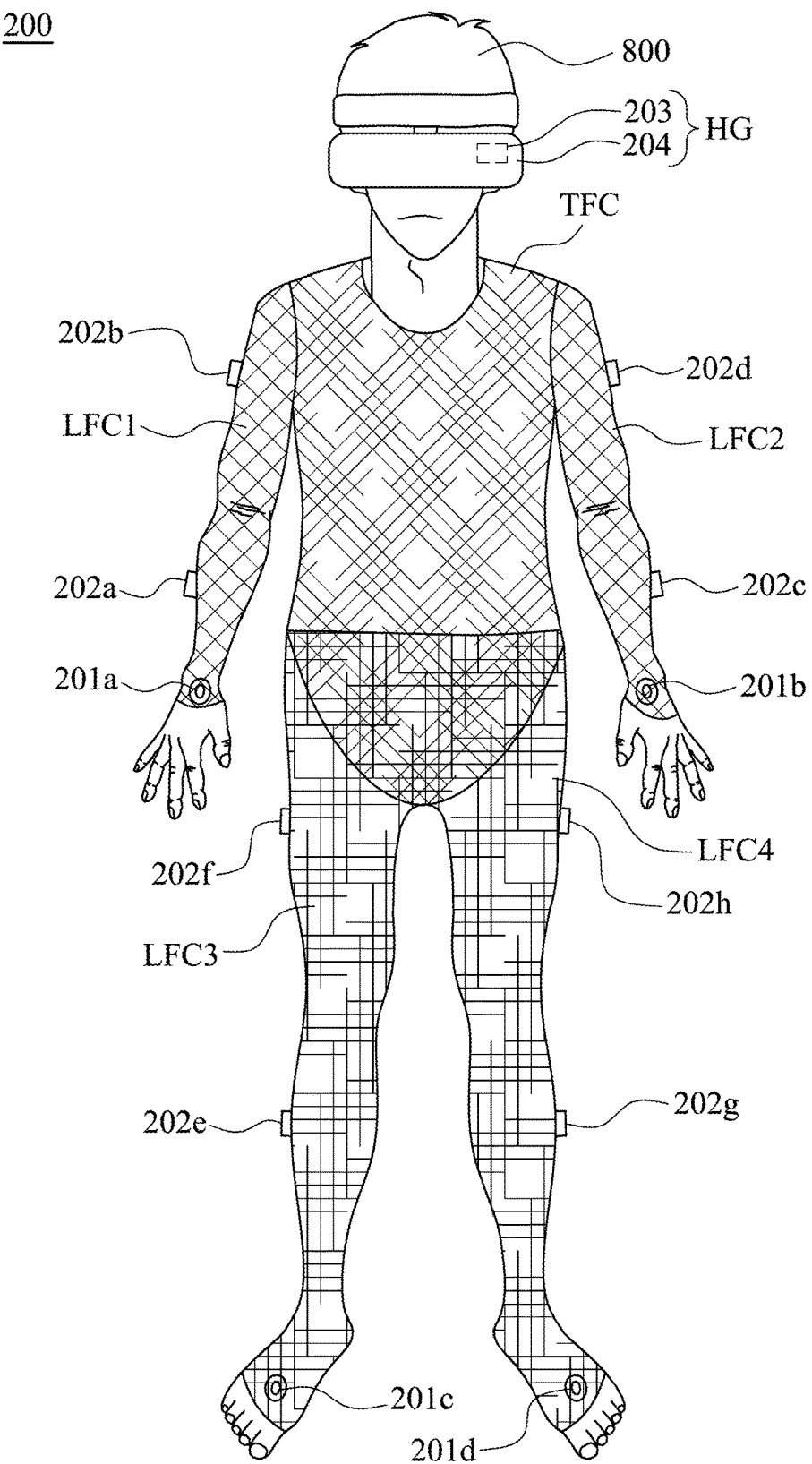
FIG. 4A is schematic diagrams of a body posture detection suit illustrated according to one embodiment of the present disclosure.
Figure 4B:
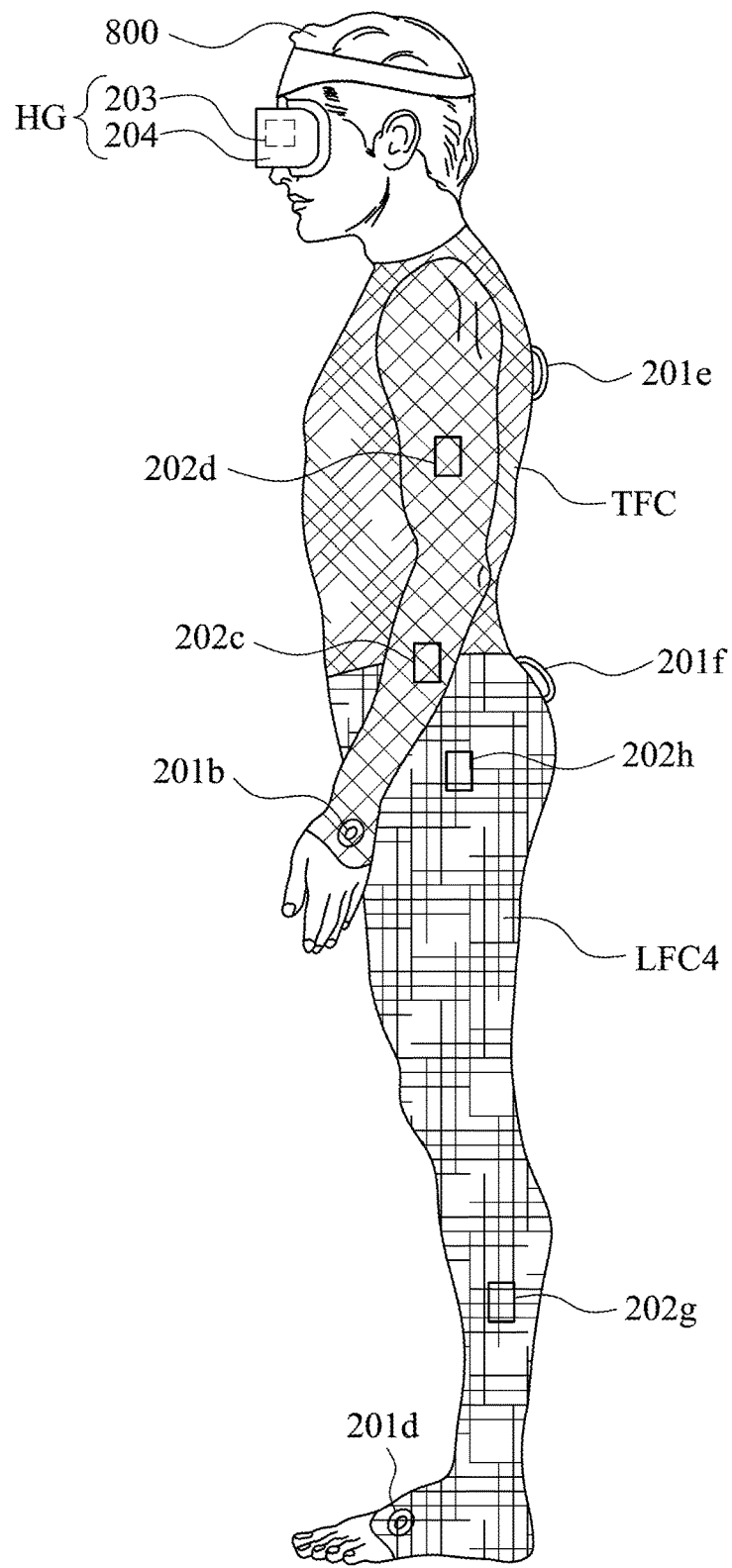
FIG. 4B is schematic diagrams of a body posture detection suit illustrated according to one embodiment of the present disclosure.

FIG. 4A and FIG. 4B are schematic diagrams of a body posture detection suit illustrated according to one embodiment of the present disclosure. In the embodiment, a user 800 is wearing a body posture detection suit 200. The body posture detection suit 200 comprises a headgear HG, a torso fitting component TFC, and four limb fitting components LFC1-LFC4. The headgear HG comprises a processor 203 and a display 204. The processor 203 is settled inside the headgear HG and the display 204 is settled toward to the user's face. The torso fitting component TFC covers the user's torso adequately, and the limb fitting components LFC1-LFC4 wrap limbs of the user 800, respectively.

In the embodiment, four inertial measurement units 201a-201d are disposed on the limb fitting components LFC1-LFC4 respectively, near critical nodes (e.g., center points or end points) of the four limbs of the user 800. The inertial measurement units 201a-201d are configured to detect orientation vectors of the user's limbs. Two inertial measurement units 201e-201f are disposed on the torso fitting component TFC, along the user's spine. The inertial measurement units 201e-201f are configured to detect orientation vectors of the user's torso.

In the embodiment, ultrasonic transceivers 202a-202b are disposed on the limb fitting component LFC1. Each portion (e.g., a right wrist, a right lower arm and a right upper arm) of the user's right arm is disposed with one ultrasonic transceiver. Ultrasonic transceivers 202c-202d are disposed on the limb fitting component LFC2. Each segment of the user's left arm is disposed with one ultrasonic transceiver. Ultrasonic transceivers 202c-202d are disposed on different limb portions (e.g., a right wrist, a right lower arm and a right upper arm) of the human body. The current gesture determined by the processor indicates a relative position between the different limb portions. Ultrasonic transceivers 202e-202f are disposed on the limb fitting component LFC3. Each portion of the user's right leg is disposed with one ultrasonic transceiver. Ultrasonic transceivers 202g-202h are disposed on the limb fitting component LFC4. Each portion of the user's left leg is disposed with one ultrasonic transceiver. In an embodiment, the ultrasonic waves generated by the ultrasonic transceivers 202a-202h are unique and different from each other (e.g., the ultrasonic waves are broadcasted at different sound frequencies, different amplitudes or different waveform pattern), so that the ultrasonic transceivers 202a-202h are able to distinguish origins of these ultrasonic waves. In another embodiment, the ultrasonic waves are generated in a time-division way during different time periods with a similar format (e.g., in frequency, amplitude or waveform pattern), so that the ultrasonic transceivers are able to distinguish origins of these ultrasonic waves according to a time division of the received ultrasonic wave.

In the embodiment, the processor 203 settled in the headgear HG is in communication with these inertial measurement units 201a-201f and the ultrasonic transceivers 202a-202h. The processor 203 is configured to fetch instructions from internal or external memories and to perform following processes according to the instructions. Similar to the embodiment of FIG. 1, the processor 203 can retrieve the orientation vectors from the inertial measurement units 201a-201f and measure the relative distances among the ultrasonic transceivers 202a-202h. Next, the processor 203 can calculate rotation angles of each joint that the suit covers according to the orientation vector, the relative distances and also kinematic constraints of these joints. The kinematic constraints of these joints are utilized to exclude unreasonable rotation angles between these joints from consideration.

By importing kinematic constraints of these joints into calculation, the processor 203 can generate a result indicating a current posture that the user's body performs.

In the embodiment, the display 204 is electrically coupled to the processor 203. The processor 203 is further configured to send information about a simulated environment to the display 204 so that the display 204 can output a scenario of the simulated environment to the user 800 based on the information. It should be noted, said simulated environment can be a computer technology that generates realistic images, sounds and other sensations to simulate a virtual or imaginary environment. For example, the simulated environment can be a virtual reality (VR) space, augmented reality (AR) space or mixed reality (MR) space. In one case, the scenario being provided to the user 800 represents a partial view of the simulated environment. An avatar is provided in the scenario to simulate the user's presence in the simulated environment. The processor 203 can send information regarding the user's current posture to the display 204, and the avatar in the scenario will perform a posture according to the information. Therefore, the result generated by the processor 203 can be utilized to simulate the user's action in the simulated environment effectively.

Figure 5:
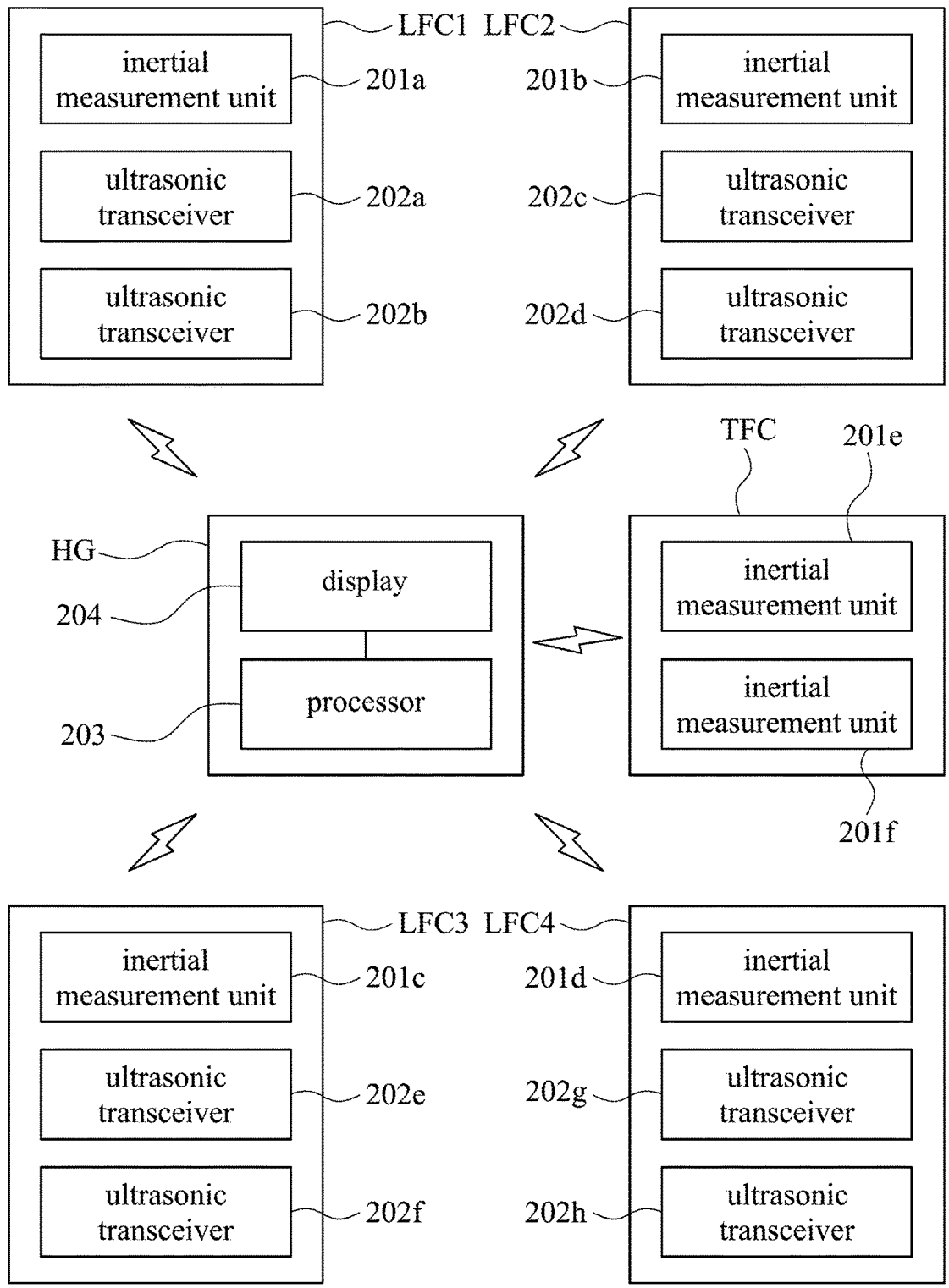
FIG. 5 is a schematic diagram of a body posture detection suit illustrated according to the embodiment of FIG. 4A and FIG. 4B.

FIG. 5 is a schematic diagram of a body posture detection suit illustrated according to the embodiment of FIG. 4A and FIG. 4B. In the embodiment, a connection among the components of the body posture detection suit 200 is represented in a series of blocks. As shown in FIG. 5, the headgear HG comprises the processor 203 and the display 204. The inertial measurement unit 201a and the ultrasonic transceivers 202a-202b are disposed on the limb fitting components LFC1. The inertial measurement unit 201b and the ultrasonic transceivers 202c-202d are disposed on the limb fitting components LFC2. The inertial measurement unit 201c and the ultrasonic transceivers 202e-202f are disposed on the limb fitting components LFC3. The inertial measurement unit 201d and the ultrasonic transceivers 202h-202g are disposed on the limb fitting components LFC4. The inertial measurement units 201e-201f are disposed on the torso fitting component TFC. In the embodiment, all these inertial measurement units and ultrasonic transceivers are in communication with the processor for information exchange. As described in foregoing embodiment, the processor 203 is configured to retrieve the orientation vector and the relative distances and also consider the kinematic constraints of these joints, to calculate rotation angles of each joint of the user, and to generate the current posture that the user performs. By retrieving the information of the current posture, the posture that the user performs can be displayed by the display 204 in the simulated environment.

Figure 6:
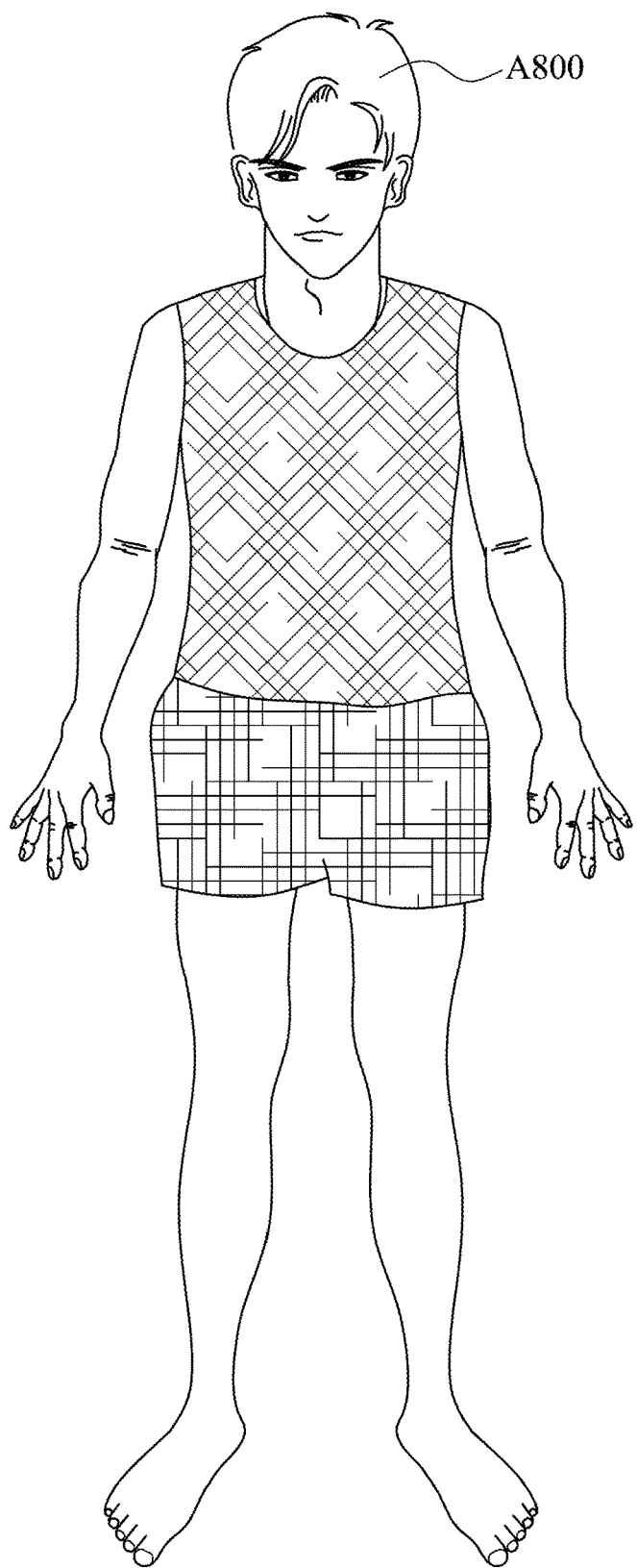
FIG. 6 is a schematic diagram of an avatar illustrated according to the embodiment of FIG. 4A.

FIG. 6 is a schematic diagram of an avatar A800 illustrated according to the embodiment of FIG. 4A. As described in the embodiment of FIG. 4A, with the information of the current posture that the user's body performs, the 204 can output the scenario of the simulated environment to the user. FIG. 6 shows an example of the avatar A800 being displayed in the scenario of the simulated environment. It is clear that the avatar A800 performs a posture in consistent to the current posture that the user 800 performs in FIG. 4A.

Figure 7:
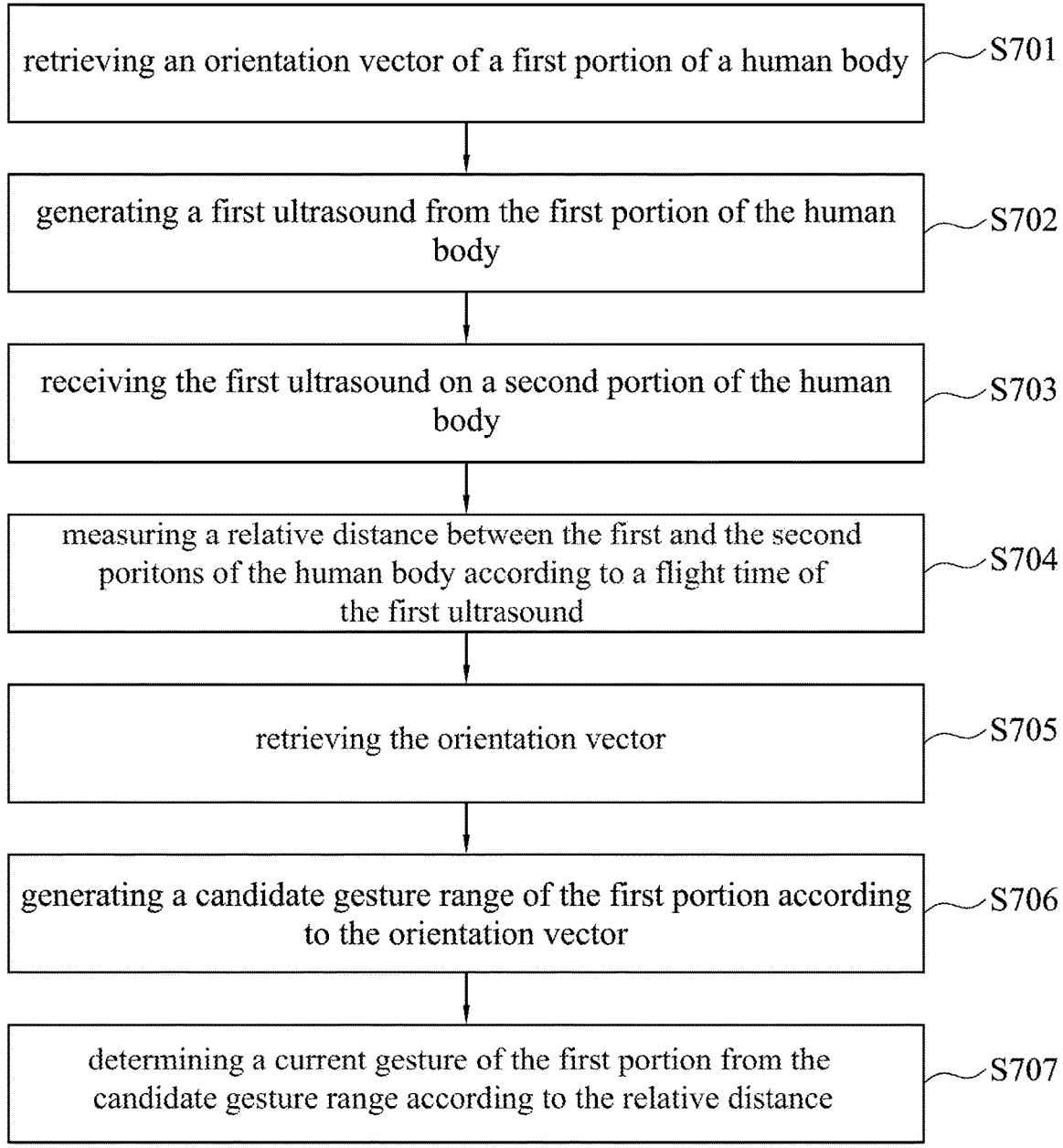
FIG. 7 is a flow chart of a body posture detection method illustrated according to some embodiments of the present disclosure.

FIG. 7 is a flow chart of a body posture detection method illustrated according to some embodiments of present disclosure. In the embodiment, the body posture detection method 700 can be executed by the body posture detection system 100 or the body posture detection suit 200 shown in foregoing embodiments, and the references to the embodiments are herein incorporated. In the embodiment, the steps of the body posture detection method 700 will be listed and explained in detail in following segments.

Step S701: retrieving, by an inertial measurement unit, an orientation vector of a first portion of a human body. As described in the embodiment of FIG. 1 and FIG. 2, the inertial measurement unit 101 deployed on an end point of the user's arm is configured to detect the orientation vector of the arm. As described in the embodiment of FIG. 4A and FIG. 4B, the inertial measurement units 201a-201d are disposed on the limb fitting components LFC1-LFC4 respectively to detect the orientation vectors of the user's limbs.

Step S702: generating, by a first ultrasonic transceiver, a first ultrasound from the first portion of the human body. As described in the embodiment of FIG. 1 and FIG. 2, the first ultrasonic transceiver 102a deployed on the first reference point is configured to generate the first ultrasonic wave. As described in the embodiment of FIG. 4A and FIG. 4B, the ultrasonic transceivers 202a-202h deployed on the user's limbs are configured to generate ultrasonic waves that are unique among each other.

Step S703: receiving, by a second ultrasonic transceiver, the first ultrasound on a second portion of the human body. As described in the embodiment of FIG. 1 and FIG. 2, the second ultrasonic transceiver 102b deployed on the second reference point is configured to receive the first ultrasonic wave.

Step S704: measuring, by the processor, a relative distance between the first and the second portions of the human body according to a flight time of the first ultrasound. As described in the embodiment of FIG. 1 and FIG. 2, when the sending time of the first ultrasonic wave is known, the processor 103 can measure the relative distance between the first ultrasonic transceiver 102a and the second ultrasonic transceiver 102b when the first ultrasonic wave is received. As described in the embodiment of FIG. 4A and FIG. 4B, the relative distances between pairs of the ultrasonic transceivers 202a-202h can be measured by the processor 103.

Step S705: retrieving, by a processor, the orientation vector and the relative distance. As described in the embodiment of FIG. 1 and FIG. 2, the processor 103 is configured to retrieve the orientation vector from the inertial measurement unit 101. As described in the embodiment of FIG. 4A and FIG. 4B, the processor 203 is configured to retrieve the orientation vectors from the inertial measurement unit 201a-201f.

Step S706: generating, by the processor, a candidate gesture range of the first portion according to the orientation vector. As described in the embodiment of FIG. 1, FIG. 2, FIG. 3A-3D, the processor 103 is configured to generate the candidate gesture range CGR of the user's limb. It is noted that the candidate gesture range is a data set contains several potential possibilities that the user's limb may have positioned. As described in the embodiment of FIG. 4A, FIG. 4B, and FIG. 5, the processor 203 is configured to calculate candidate gesture ranges corresponding to all the user's limbs according to the orientation vectors. In some cases, kinematic constraints of the user's joints will be introduced by the processor 103 to narrow down possible results.

Step S707: determining, by the processor, a current gesture of the first portion from the candidate gesture range according to the relative distance. As described in the embodiment of FIG. 1, FIG. 2, and FIG. 3A-3D, on the basis that the lengths of arms of the user are known, the processor 103 can determine the current gesture, such as gestures CG1-CG3, in accordance with the distances (distance DST1-DST3) measured by the second ultrasonic transceiver 102b from the candidate gesture range CGR. As described in the embodiment of FIG. 4A, FIG. 4B, and FIG. 5, the processor 203 is configured to generate a signal current gesture of the user's body from a combination of those candidate gesture ranges.

As described in foregoing embodiments, present disclosure provides an effective approach for detecting positions of limbs with a combination of ultrasonic transceivers and IMUs. Even when the system is being applied in a building constructed by reinforcement steels that may influence accuracy of IMUs, the approach is still applicable.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A body posture detection system, comprising:
   an inertial measurement unit, mounted on a first portion of a human body, configured to sense an orientation vector of the first portion;
   an ultrasonic module, comprising a first ultrasonic transceiver mounted on the first portion and a second ultrasonic transceiver mounted on a second portion of the human body; and
   a processor, communicatively connected with the inertial measurement unit and the ultrasonic module, wherein the processor is configured to generate a plurality of candidate gestures of the first portion shared an identical angle between a gravitation and the orientation vector according to the orientation vector sensed by the inertial measurement unit and
   the processor is configured to measure a distance between the first portion and the second portion according to an ultrasound transmitted between the first ultrasonic transceiver and the second ultrasonic transceiver;
   wherein the processor is further configured to eliminate a plurality of impossible gestures from the candidate gestures according to the distance and a human kinetic constraint, in order to determine a current gesture.

2. The body posture detection system of claim 1, wherein the first portion is a first limb portion of the human body, and the candidate gestures are generated by the processor according to the orientation vector and a body kinematic constraint of the first limb portion.

3. The body posture detection system of claim 2, wherein the second portion is a torso portion of the human body, and the current gesture determined by the processor indicates a position and a direction of the first limb portion relative to the torso portion.

4. The body posture detection system of claim 2, wherein the second portion is a second limb portion of the human body, and the current gesture determined by the processor indicates a relative position between the first limb portion and the second limb portion.

5. The body posture detection system of claim 1, the ultrasound is generated by the first ultrasonic transceiver and transmitted to the second ultrasonic transceiver, or generated by the second ultrasonic transceiver and transmitted to the first ultrasonic transceiver.

6. The body posture detection system of claim 1, the distance is measured by the processor according to a flight time of the ultrasound.

7. A body posture detection suit, comprising:
   a torso fitting component;
   a plurality of limb fitting components, connected to the torso fitting component;
   a plurality of inertial measurement units, disposed on the torso fitting component and the limb fitting components respectively, configured to sense orientation vectors of the torso fitting component or the limb fitting components;
   a plurality of ultrasonic transceivers, disposed on multiple reference points on the limb fitting components, configured to send ultrasounds and to receive the ultrasounds respectively; and
   a processor, in communication with the inertial measurement units and the ultrasonic transceivers, configured to measure distances among these reference points according to flight times of the ultrasounds, retrieve the orientation vectors, generate a plurality of current gestures of the limb fitting components shared an identical angle between a gravitation and the orientation vector according to the orientation vector, and
   eliminate a plurality of impossible gestures from the candidate gestures according to the distance and a human kinetic constraint in order to determine a current gesture of the limb fitting components in combination with the torso fitting component.

8. The body posture detection suit of claim 7, wherein the inertial measurement units are disposed on ends of the limb fitting components or disposed along a proximal axis of the torso fitting component.

9. The body posture detection suit of claim 7, wherein the reference points are distributed on segments of the limb fitting components.

10. The body posture detection suit of claim 7, further comprising:
    a head mounted display, in communication with the processor, configured to output a scenario of a simulated environment that an avatar is presented therein, and to display a gesture of the avatar in the scenario according to the current gesture of the torso fitting component and the limb fitting components.

11. A body posture detection method, applied on a human body, wherein the body posture detection method comprises:
    sensing, by an inertial measurement unit, an orientation vector of a first portion of the human body;
    measuring, by a processor, a distance between a first portion of the human body and a second portion of the human body according to an ultrasound transmitted between a first ultrasonic transceiver mounted on the first portion and a second ultrasonic transceiver mounted on the second portion;
    generating, by the processor, a plurality of candidate gestures of the first portion shared an identical angle between a gravitation and the orientation vector according to the orientation vector sensed by the inertial measurement unit; and
    eliminating a plurality of impossible gestures from the candidate gestures according to the distance and a human kinetic constraint, in order to determine a current gesture.

12. The body posture detection method of claim 11, wherein the first portion is a first limb portion of the human body, the candidate gestures are generated by the processor according to the orientation vector and a body kinematic constraint of the first limb portion.

13. The body posture detection method of claim 12, wherein the second portion is a torso portion of the human body, the current gesture determined by the processor indicates a position and a direction of the first limb portion relative to the torso portion.

14. The body posture detection method of claim 12, wherein the second portion is a second limb portion of the human body, the current gesture determined by the processor indicates a relative position between the first limb portion and the second limb portion.

15. The body posture detection method of claim 11, the ultrasound is generated by the first ultrasonic transceiver and transmitted to the second ultrasonic transceiver, or generated by the second ultrasonic transceiver and transmitted to the first ultrasonic transceiver.

16. The body posture detection method of claim 11, the distance is measured by the processor according to a flight time of the ultrasound.

* * * * *